(12) United States Patent
Lo

(10) Patent No.: US 6,462,814 B1
(45) Date of Patent: Oct. 8, 2002

(54) BEAM DELIVERY AND IMAGING FOR OPTICAL PROBING OF A DEVICE OPERATING UNDER ELECTRICAL TEST

(75) Inventor: William K. Lo, San Jose, CA (US)

(73) Assignee: Schlumberger Technologies, Inc., San Jose, CA (US)

( * ) Notice: Subject to any disclaimer, the term of this patent is extended or adjusted under 35 U.S.C. 154(b) by 0 days.

(21) Appl. No.: 09/526,979

(22) Filed: Mar. 15, 2000

(51) Int. Cl.[7] .............................................. G01N 21/00
(52) U.S. Cl. .................................. 356/237.2; 356/237.5
(58) Field of Search ........................... 356/237.2–237.5

(56) References Cited

U.S. PATENT DOCUMENTS

| | | | |
|---|---|---|---|
| 3,999,864 A | * 12/1976 | Mutter | 356/212 |
| 4,615,620 A | * 10/1986 | Noguchi et al. | 356/378 |
| 4,618,819 A | 10/1986 | Mourou et al. | |
| 4,681,449 A | 7/1987 | Bloom et al. | |
| 4,706,019 A | 11/1987 | Richardson | |
| 4,758,092 A | 7/1988 | Heinrich et al. | |
| 4,846,184 A | * 7/1989 | Comment et al. | 128/633 |
| 4,857,836 A | 8/1989 | Söelkner | |
| 4,908,568 A | 3/1990 | Soelkner | |
| 4,927,254 A | 5/1990 | Kino et al. | |
| 4,965,441 A | 10/1990 | Picard | |
| 5,022,743 A | 6/1991 | Kino et al. | |
| 5,042,302 A | 8/1991 | Soelkner | |
| 5,122,653 A | 6/1992 | Ohki | |
| 5,132,526 A | 7/1992 | Iwasaki | |
| 5,140,164 A | 8/1992 | Talbot et al. | |
| 5,150,182 A | 9/1992 | Capps et al. | |
| 5,164,664 A | 11/1992 | Soelkner | |
| 5,210,487 A | * 5/1993 | Takahashi et al. | 324/158 |
| 5,272,434 A | 12/1993 | Meyrueix et al. | |
| 5,381,236 A | 1/1995 | Morgan | |
| 5,389,783 A | 2/1995 | Shionoya et al. | |
| 5,394,098 A | 2/1995 | Meyrueix et al. | |
| 5,475,316 A | 12/1995 | Hurley et al. | |
| 5,508,805 A | 4/1996 | Muranishi et al. | |
| 5,535,052 A | 7/1996 | Jörgens | |
| 5,537,247 A | 7/1996 | Xiao | |
| 5,640,539 A | * 6/1997 | Goishi et al. | 395/500 |
| 5,754,298 A | 5/1998 | Falk | |
| 5,872,360 A | 2/1999 | Paniccia et al. | |
| 5,880,828 A | * 3/1999 | Nakamura et al. | 356/237.3 |
| 5,905,577 A | * 5/1999 | Wilsher et al. | 356/448 |
| 6,163,159 A | * 12/2000 | Seyama | 324/751 |

OTHER PUBLICATIONS

Black et al., "Optical Sampling of GHz Charge Density Modulation in Silicon Bipolar Junction Transistors," *Electronics Letters*, 1987, 23(15:783–784.

Cogswell and Sheppard, "Confocal differential interference contrast (DIC) microscopy: including a theoretical analysis of conventional and confocal DIC imaging," *J. Microscopy*, 1990, 165(1):81–101.

(List continued on next page.)

Primary Examiner—Michael P. Stafira
(74) Attorney, Agent, or Firm—Fish & Richardson, P.C.

(57) ABSTRACT

Methods and apparatus for optically probing an electrical device while the device is operating under control of a tester of the kind that applies test vectors and that has a test head in which the device can be mounted. An optical probe system has a light delivery and imaging module that is configured to be docked to a test head and that has imaging optics and a fine scanner. An optical processing subsystem can generate an incoming beam of light to illuminate the device through an optical fiber to a fiber end in the module. The fiber end is mounted in a fixed position on the optical axis of the imaging optics, and the fiber end and imaging optics are mounted in a fixed position to the platform of the fine scanner. Operating the fine scanner moves the fiber end, the imaging optics, the optical axis, and the focal point as a rigid unit.

22 Claims, 4 Drawing Sheets

OTHER PUBLICATIONS

Corle et al., "Depth response of confocal optical microscopes," *Optics Letters*, 1986, 11(12):770–772.

Heinrich et al., "Picosecond Backside Optical Detection of Internal Signals in Flip–Chip Mounted Silicon VLSI Circuits," *Microelectronic Engineering*, 1992, 16:313–324.

Hemenway et al., "Optical Detection of Charge Modulation in Silicon Integrated Circuits Using a Multimode Laser–Diode Probe," *IEEE Electron Device Letters*, 1987, EDL–8(8):344–346.

Juškaitis and Wilson, "Differential confocal scanning microscope with a two–mode optical fiber," *Applied Optics*, 1992, 31(7):898–902.

Seliger et al., "A Study of Backside Laser–Probe Signals in Mosfets," 1995.

Talbot et al., Failure Analysis, "Bringing Mechanical Probing Out of the Stone Age," *Evaluation Engineering*, 1995.

Wilsher and Lo, "Practical Optical Waveform Probing of Flip–Chip CMOS Devices," ITC International Test Conference, *IEEE*, 1999, pp. 932–939.

* cited by examiner

BEAM DELIVERY AND IMAGING FOR OPTICAL PROBING OF A DEVICE OPERATING UNDER ELECTRICAL TEST

BACKGROUND OF THE INVENTION

The invention relates to systems and methods for optical probing of an electrical device such as an integrated circuit.

Electrical devices, such as integrated circuits (ICs), may fail for a variety of reasons. Particular defects within an electrical device may be identified by optical probing of the device as the device is being conditioned by test equipment capable of exercising the device under normal clock operating rates. ATE (automated test equipment) production testers combine device level biasing with sophisticated software for delivering test signals (vectors) to the device at normal operating rates. A variety of optical techniques have been described for evaluating the performance of an electrical device under test (DUT). For example, optical techniques which detect charge density variations in an electrical DUT may be used to monitor logic states and signal levels at internal nodes within the electrical device. These techniques are particularly useful for monitoring and diagnosing the performance of circuit nodes that are not readily accessible to non-optical probes. For example, the device side of many ICs (so-called flip-chip devices) are inaccessible to probes. Thus, testing and debugging of such devices must be done from the back side, using techniques described, for example, in K. R. Wilsher and W.K. Lo, Practical Optical Waveform Probing of Flip-Chip CMOS Devices, Proceedings, ITC International Test Conference, paper 35.1, pp. 932–39 (hereafter, "Wilsher & Lo"), which is incorporated herein by reference.

SUMMARY OF THE INVENTION

In general, in one aspect, the invention provides an optical probe system for optically probing an electrical device while the device is operating under control of a tester of the kind that generates and applies a sequence of test vectors to the device and that has a test head in which the device can be mounted. The optical probe system has a light delivery and imaging module that is configured to be docked to a test head and that has imaging optics and a fine scanner. The optical probe system also has an optical processing subsystem that can generate an incoming beam of light to illuminate the device; a data processing subsystem that can generate control signals for the module and that can transmit control signals to the module; and an optical fiber connected to transmit the incoming beam from the optical processing subsystem to a fiber end in the module. The fine scanner has a frame and a platform and can receive control signals from the data processing subsystem to move the platform relative to the frame. The fiber end is mounted in a fixed position on the optical axis of the imaging optics so that light emitted from the fiber end is focused at a focal point in a focal plane by the imaging optics, and the fiber end and imaging optics are mounted in a fixed position to the platform of the fine scanner, whereby operating the fine scanner moves the fiber end, the imaging optics, the optical axis, and the focal point as a rigid unit.

Advantageous implementations can includes one or more of the following features. The system further includes a coarse stage having a frame and a platform, the platform being connected to the fine scanner in a fixed relationship, the coarse stage being coupled to receive control signals from the data processing subsystem to move the platform of the coarse stage. The fine scanner can move the imaging optics and the fiber end in an XY plane perpendicular to the optical axis and in a Z direction parallel to the optical axis; and the fine scanner is so positioned in the module that the focal point moves in a focal plane intersecting the device when the fine scanner moves the fiber end in the XY plane and the module is docked to the test head. The fiber is a polarization-maintaining, single-mode fiber; the incoming beam of light is monochromatic and linearly polarized; and the fiber end is polished so that the beam is spatially filtered. The focal point and the fiber end are conjugate focal points of the imaging optics; and the fiber end defines an aperture that delivers light to and from the imaging optics, whereby light delivered to the imaging optics through the aperture and light reflecting from the focal plane passes through the aperture. The optical processing subsystem includes a polarizing beam splitter configured to pass light from a light source with a first polarization and to reflect light with a different polarization toward a detector, and it is configured to deliver the light from the beam splitter to the fiber; and the imaging optics have a quarter-wave plate on the optical axis between the fiber end and the focal point. The fiber is a single-mode fiber, and the incoming beam of light is monochromatic. The incoming beam of light is produced by a pulsed laser and has a near infrared wavelength.

The fiber is a polarization-maintaining, single-mode fiber; the incoming beam of light is monochromatic and linearly polarized; the fiber end is polished so that the beam is spatially filtered; the system further comprises a coarse stage having a frame and a platform, the platform being connected to the fine scanner in a fixed relationship, the course stage being coupled to receive control signals from the data processing subsystem to move the platform of the coarse stage; the focal point and the fiber end are conjugate focal points of the imaging optics; the fiber end defines an aperture that delivers light to and from the imaging optics, whereby light delivered to the imaging optics through the aperture and light reflecting from the focal plane passes through the aperture; the optical processing subsystem comprises a polarizing beam splitter configured to pass light from a light source with a first polarization and to reflect light with a different polarization toward a detector, the optical processing subsystem being configured to deliver the light from the beam splitter to the fiber; and the imaging optics comprise a quarter-wave plate on the optical axis between the fiber end and the focal point. The optical processing subsystem and the data processing subsystem are housed in a common probe system chassis.

In general, in another aspect, the invention provides a method for optically probing an electrical device. The method includes operating the device; providing imaging optics, the imaging optics having an optical axis and a focal point on the optical axis, the imaging optics positioned in a spatial relationship to the device so that the focal point intersects the device; providing an aperture on the optical axis through which light is delivered to the imaging optics; moving the aperture, the optical axis, and the imaging optics as a rigid unit to move the focal point to a reference point in the device; and providing a beam of light to the aperture and receiving reflected light from the device.

Advantageous implementations can includes one or more of the following features. The device is operated under a repeating sequence of test vectors. The method further includes raster scanning the focal point over an area of the device while illuminating the device with light delivered through the aperture. The method further includes placing the aperture at a conjugate to the focal point and receiving the reflected light through the aperture.

In general, in another aspect, the invention provides an optical probe system for optically probing an electrical device while operating the device under control of a tester. The optical probe system has a light delivery and imaging module. The module has imaging optics, a coarse stage and a fine scanner, and is configured to be docked to a test head. The system has an optical processing subsystem operable to generate an incoming beam of light to illuminate the device; a data processing subsystem operable to generate control signals for the module and operatively coupled to transmit control signals to the module, the coarse stage and the fine scanner being coupled to receive control signals from the data processing subsystem; and an optical fiber connected to transmit the incoming beam from the optical processing subsystem to a fiber end in the module. The imaging optics have an optical axis, a focal plane, and a conjugate focal plane. A frame of the fine scanner and the imaging optics are mounted in a fixed position relative to a platform of the coarse stage, whereby operating the coarse stage moves the imaging optics, the optical axis, and the frame of the fine scanner as a unit. The fiber end is mounted on a platform of the fine scanner so that operating the fine scanner moves the fiber end in the conjugate plane and so that light emitted from the fiber end is focused in the focal plane by the imaging optics, whereby operating the coarse stage moves the fiber end, the imaging optics, the optical axis, and the focal point as a unit, and operating the fine scanner moves the fiber end and focal point relative to the imaging optics.

Advantageous implementations can includes one or more of the following features. The fine scanner can move the fiber end in an XY plane perpendicular to the optical axis and in a Z direction parallel to the optical axis; and the fine scanner is so positioned in the module that the focal point moves in a focal plane intersecting the device when the fine scanner moves the fiber end in the XY plane and the module is docked to the test head. The fiber end defines an aperture that delivers light to and from the imaging optics, whereby light delivered to the imaging optics through the aperture and light reflecting from the focal plane passes through the aperture. The optical processing subsystem includes a polarizing beam splitter configured to pass light from a light source with a first polarization and to reflect light with a different polarization toward a detector, where the optical processing subsystem is configured to deliver the light from the beam splitter to the fiber; and the imaging optics include a quarter-wave plate on the optical axis between the fiber end and the focal point.

In general, in another aspect, the invention provides a method for optically probing an electrical device. The method includes operating the device; providing imaging optics, the imaging optics having an optical axis and a focal plane, the imaging optics being positioned in a spatial relationship to the device so that the focal plane intersects the device; providing an aperture through which light is delivered to the imaging optics, positioned so that light from the aperture is focused at a focal point; moving the imaging optics in a plane parallel to the focal plane; moving the aperture relative to the imaging optics to move the focal point to a reference point in the device; and providing a beam of light to the aperture and receiving reflected light from the device.

Among the advantages that can be seen in particular implementations of the invention are the following. The beam delivery and imaging subsystem requires only a small number of components and may be of small size and low weight and can therefore be mounted quickly and easily to the test head of an ATE system in contrast to prior art systems that require the imaging module to be docked to the test head of the ATE system. The invention can achieve good imaging results because the beam delivery and imaging subsystem can be substantially decoupled from sources of vibrational noise (e.g., vacuum pumps) and can be rigidly coupled to the ATE test head. The small size of the beam delivery and imaging subsystem provides a short mechanical path (allowing little relative vibration) between the scanner optics and the DUT. The beam delivery and imaging subsystem can be made from a small number of optical elements, which can contribute to good transmission efficiency. The system can perform optical probing during parametric and functional testing of a delidded or flip-chip device mounted in an ATE tester test head.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
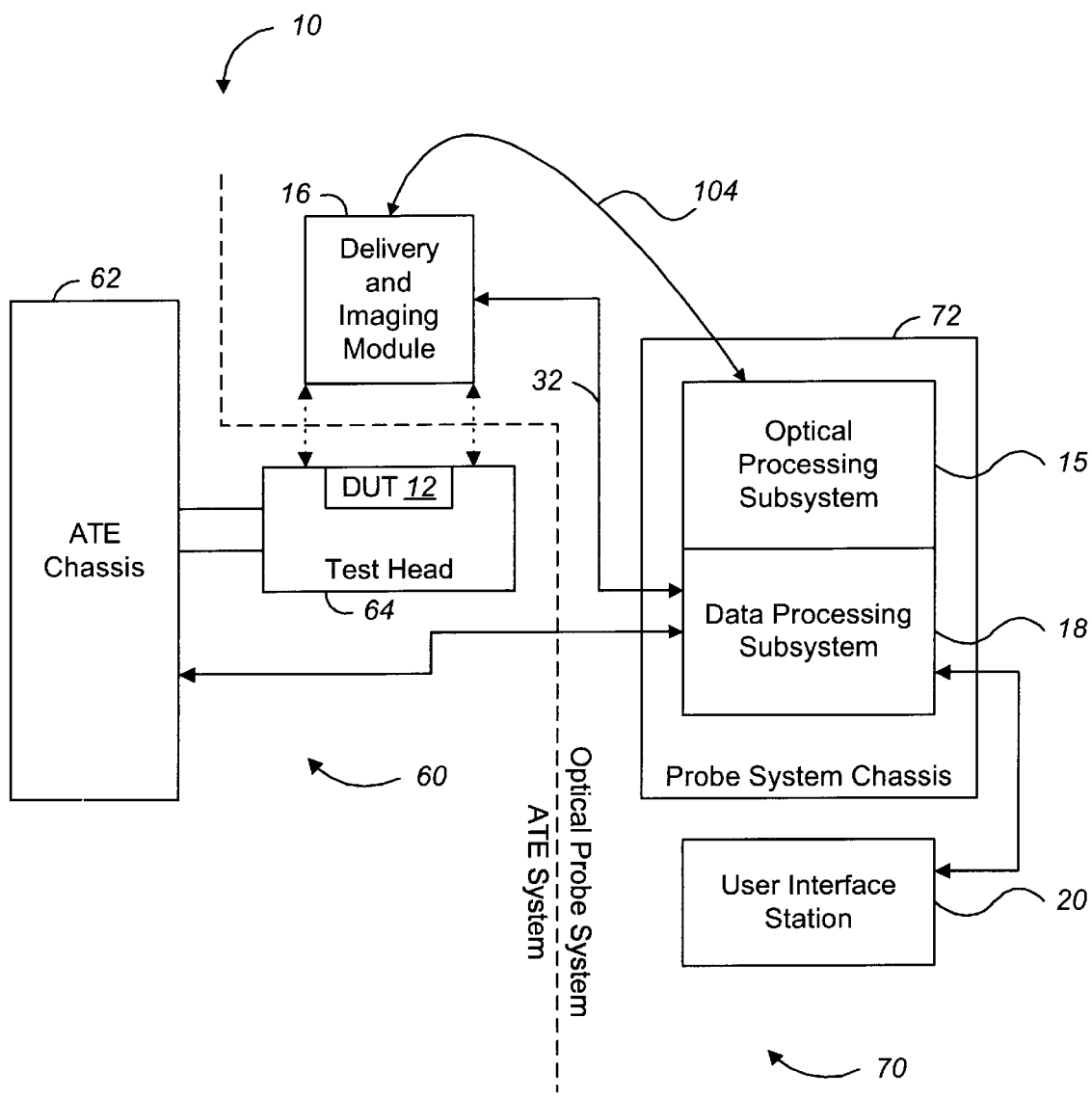
FIG. 1 is a block diagram of a system in which a circuit tester and an optical probe system are coupled and operated together to probe optically an electrical device in operation.

As illustrated in FIG. 1, an electrical device under test (DUT) 12, such as a silicon-based semiconductor device, can be tested electrically by a commercially available circuit tester (e.g., one of the ITS 9000 family of testers available from Schlumberger Technologies, Inc. of San Jose, Calif., USA), which can apply to the DUT 12 a sequence of test vectors of a test program. While the DUT is being exercised by the tester, by the repeated application of a pattern of test vectors, for example, the DUT can be probed by an optical probe system 70, as generally described in Wilsher & Lo. More specifically, the probe system 70 has a probe system chassis 72 and user interface station 20, as are found in the commercially-available IDS 2000™ Flip-chip Probe System, available from Schlumberger Technologies, Inc. The probe system 70 also has an advantageous, lightweight delivery and imaging module 16, which receives and transmits optical signals through an optical fiber 104 coupled to an optical processing subsystem 15 in the chassis 72.

The imaging module 16 includes optics and a scanning mechanism for imaging and tracing a probe beam received through the fiber 104 across the DUT, as well as for receiving light that reflects from the DUT and transmitting it to the optical processing subsystem 15. The imaging module 16 aims or scans the probe beam at a desired location or over a desired pattern on the DUT in response to commands sent by the data processing subsystem 18 of the probe system over signal lines 32.

The data processing subsystem 18 interacts with the tester 60 to synchronize the timing of probe measurements with applied test signals and optionally to specify the test signal pattern applied to the DUT. The entire system 10 may be controlled by an operator through a graphical user interface using the user interface station 20.

Figure 2:
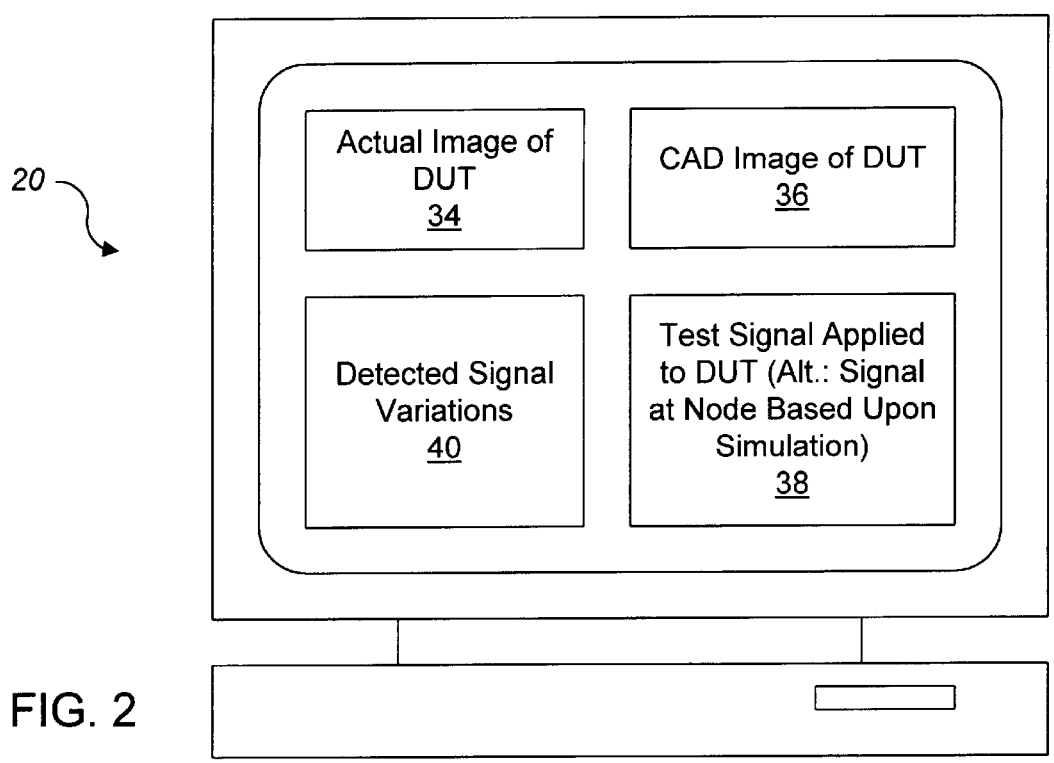
FIG. 2 is a diagrammatic view of the user interface of FIG. 1 showing different information relating to the operation of the device under test.

As illustrated in FIG. 2, the user interface station 20 operates under computer program control and can be configured to display different information relating to the operation and testing of the DUT. For example, the station 20 can be configured to display an image 34 of the actual circuit layout of the DUT, a CAD (computer aided design) image 36 of the design circuit layout of the DUT, an image 38 of the test signal pattern applied to the DUT (or an image of the signal variations that are expected to occur at a reference node as determined from a computer simulation), and an image 40 of the detected signal variations at one or more internal nodes of the DUT. System 10 can be used to produce images 34 and 40: image 34 can be produced by processing the reflection of a probe beam illuminating the DUT while tracing over it; image 40 can be produced by processing the reflection of a probe beam aimed at an internal node of the DUT while the DUT is being exercised by the tester.

In operating the system 10, a user can specify the parameters of a test signal pattern, through the station 20, for example, or through a direct operator interface to the tester. The user can then use the interface station 20 to identify or find a reference node of the DUT at which signal variations are to be detected, for example, by locating a reference node on a CAD image 36 and comparing the CAD image 36 with an image 34 of the actual circuit layout. Once the reference node has been specified, data processing subsystem 18 sends commands that direct the imaging module 16 to move to the location on the DUT corresponding to the reference node while the tester applies a specified test signal pattern to the DUT. The reflected light from the DUT is transmitted from the imaging module 16 to the probe chassis 72 where is it is converted to digital electrical signals that can be processed and analyzed by data processing subsystem 18. The data processing subsystem 18 generates and transmits to the user interface station 20 signals from which an image is produced of the signal variations induced at the reference node as a result of the applied test signal pattern.

More specifically, the system 10 can be used to detect signal variations occurring at an internal node of the DUT. Signal variations in the DUT may be detected by detecting modulation of light reflected from the DUT, as described in commonly-owned U.S. Pat. Nos. 5,872,360 and 5,905,577, which are incorporated herein by reference. In addition, the probe system 70 can also be used as a confocal laser scanning microscope system to take a series of images at many focal planes that intersect the DUT at different depths within the device, and these images may be used to create images of the three-dimensional structure of the DUT.

As indicated in FIG. 1, the imaging module 16 can be selectively mounted to the test head 64 of an ATE circuit test system 60, which has a test head 64 and a chassis 62. The imaging module 16 is lightweight, weighing about 50 pounds or less. It is physically separated from, and requires very few signal connections to, the probe system chassis 70. These include a single-mode optical fiber 104, which is enclosed within a cable, that transmits light between the imaging module 16 and the probe system chassis 72.

Figure 3:
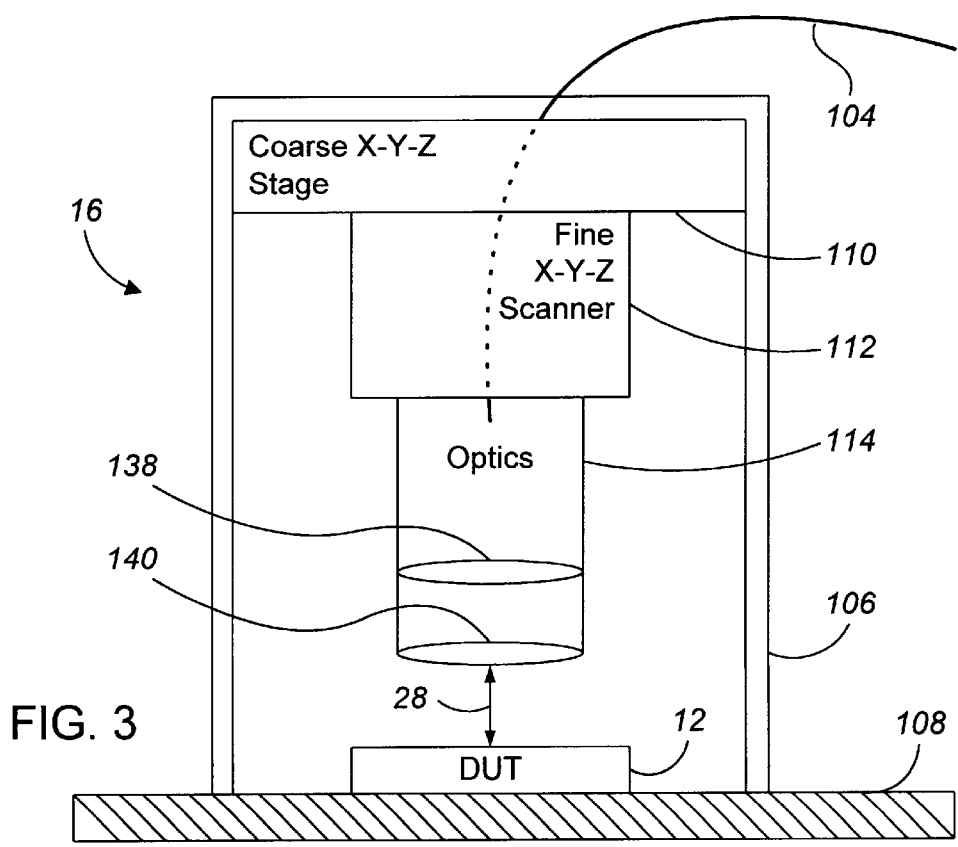
FIG. 3 is a schematic cross-sectional side view of an imaging module of the optical probe system.

As indicated in FIG. 3, the imaging module 16 includes a housing 106 that can be mounted quickly and easily to the test head 64 (FIG. 1) or to a load board 108 inside the test head—in either event, the housing 106 is mounted so the imaging module 16 is fixed relative to the DUT 12. For example, the imaging module 16 can dock to the test head with standard docking rings, or custom brackets can also be used to fix the module to the cowl of the test head 64. Because it is lightweight, the imaging module can be docked to the test head entirely by hand; or it can be mounted on a boom or a robotic manipulator and docked with manual or automatic control.

One end of the optical fiber 104 is coupled to a scan mechanism, which includes a coarse X-Y-Z stage 110 and a fine X-Y-Z scanner 112, such as a piezoelectric scanner. A stage and a scanner have a stationary part and a movable part that is fixed to the piece that is moving. When necessary to distinguish them, the stationary part will be referred to as the frame and the movable part, the platform. More specifically, the fiber is fixed to the platform of the fine X-Y-Z scanner 112, as are the optics 114, which include a collimating lens 138 and an objective lens 140. The term lens encompasses multi-element assemblies and is not limited to single-element lenses. The collimating lens 138 can be a simple lens, for example, a single-element aspheric lens such as a lens in the New Focus 57xx series, and in particular the model 5726 lens, which are available from New Focus, Inc. of Santa Clara, Calif. The objective lens 140 can be a Nikon A3717 100x lens for imaging through silicon. However, the fixed axial illumination used in this illustrated design allows the objective lens to be of a simpler, custom design.

Light delivered through the fiber 104 is focused by optics 114 to form probe beam 28, which is focused to a point on or in the DUT. The coarse X-Y-Z stage 110 can move the probe beam 28 over an area of about 1 inch by 1 inch in the X-Y plane (substantially parallel to focal plane) and about 0.5 inch in the Z direction (substantially normal to the focal plane). The coarse stage 110 can be built using Newport 423 series stages with motorized drives. Three in a stacked configuration can give X-Y-Z travel with resolution of +/−1 im. The fine X-Y-Z scanner 112 can move the beam over an area of about 200 im by 200 im in the X-Y plane and about 10 im in the Z direction. The achievable resolution/repeatability is about +/−10 nm in X, Y and +/−1 nm in Z. A piezoelectric fine X-Y-Z scanner, such as the Physik Instrumente Model P-527.3 Multi-axis Piezo Flexure NanoPositioner, can scan at a speed of about 100 scan lines per second, which has built-in sensors for closed loop control.

As can be seen from this description, the imaging module 16 has only a small number of components and so can be of small size and weight, which allows it to be mounted to the test head of a circuit tester. This also allows the mechanical path length between the DUT and optics 114 to be kept short, and thereby allows vibration-induced noise in the reflected light signal to be significantly reduced.

Figure 4:
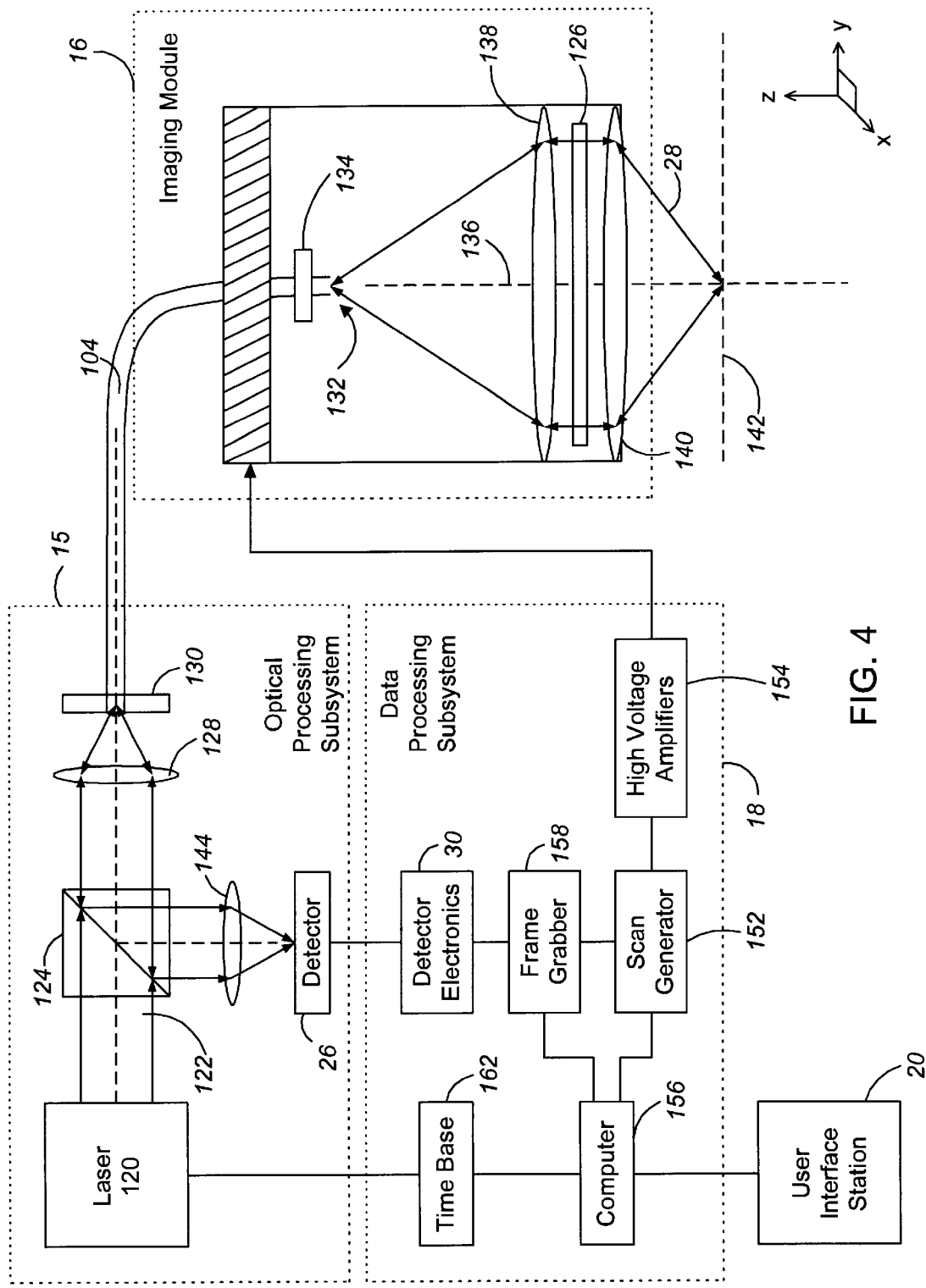
FIG. 4 is a detailed block diagram of the optical probe system.

As shown in detail in FIG. 4, the optical processing subsystem 15 includes a laser 120, which produces a monochromatic, linearly polarized (i.e., plane polarized), and collimated beam of light 122. In one implementation, the laser 120 is a mode-locked laser operating at a repetition rate of about 100 MHz with a near infrared wavelength of 1064 nm (nanometers) and a pulse width of about 35 picoseconds. The wavelength spread of such a laser is on the order of 1 nm spread. Laser 120 may use a half-wave plate and a polarizer for controlling the polarization of beam 122. Beam 122 is incident from the left on a polarizing beam splitter 124, which is configured to transmit beam 122. The linearly polarized beam is focused by a fiber coupling lens 128 onto one end of a polarization-maintaining, single-mode optical fiber 104. The beam diameter and focal length of lens 128 are selected to couple the focused beam efficiently into the fiber, which may have a numerical aperture of about 0.1. A fiber coupler 130 precisely aligns fiber 104 with the focused beam. Alternatively, a coupling lens bonded to one end of the fiber cable can be used to align the fiber with the beam.

The linearly polarized beam travels through the fiber and emerges at an end 132 of the fiber where the fiber cable is mounted to the imaging module 16. It is advantageous to cleave and polish the fiber end 132 so that the linearly polarized beam is spatially filtered, whereby the linearly polarized light that emerges has the characteristics of a beam that has passed through a pin hole aperture formed in a conventional aperture plate. A fiber aligner 134 positions the fiber end 132 relative to an optical axis 136.

A fiber coupling lens 138 collimates the linearly polarized light, a quarter-wave plate 126 converts the polarization of the collimated linearly polarized light to circularly polarized light and an objective lens 140 refocuses the resulting circularly polarized light to form probe beam 28 which is directed to a focal point on a focal plane 142. The optics are formed and positioned so that the focal plane 142 intersects the DUT. Objective lens 140 collects light from the focal point on focal plane 142 that reflects from the DUT, passes the circularly polarized reflected light through quarter-wave plate 126 which converts the circularly polarized reflected light to linearly polarized reflected light which is rotated about 90° relative to the polarization of initial beam 122, and fiber coupling lens 138 focuses the resulting linearly polarized reflected light into end 132 of the fiber 104. Use of the quarter-wave plate 126 is optional, as other means can be used to separate the incoming and outgoing beams; however, use of the quarter-wave plate 126 allows incoming and outgoing beams to be separated using polarization control, which increases the transmission efficiency of the optical system. Polarization control can also be implemented in other ways, such as by use of a Faraday Rotator.

The fiber 104 has a limited acceptance angle and a small core diameter through which light may be introduced. End 132 of the fiber is located in a plane that is conjugate to focal plane 142. The focal point on focal plane 142 and end 132 are conjugate focal points. Light that enters end 132 of the fiber is substantially limited to light from the focal point on focal plane 142 that reflects from the DUT; light reflected from regions of the DUT outside of the focal point on focal plane 142 is substantially blocked as a result of the limited acceptance angle and small core diameter of the fiber 104. Typical single mode fibers for 1064 nm wavelength have acceptance half angles of about 6 degrees and core diameters of about 5 microns. Fiber coupling lens 128 collimates the linearly polarized reflected light. Polarizing beam splitter 124 reflects the linearly polarized reflected light toward a detector coupling lens 144, which focuses the linearly polarized reflected light into a beam onto detector 26, which converts the optical signal to an electrical one.

The electrical signal is transmitted to detector electronics 30 in the data processing subsystem 18, which also includes a scan generator 152, high voltage amplifiers 154, a computer 156 with a frame grabber 158 and a time base board 162. The output of detector 26 is amplified by detector electronics 30 and digitized by frame grabber 158 in computer 156. The digitized intensity of the detector signal may be processed by programs running in the computer 156 and displayed on station 20. Reflected light intensity variations that are detected as the DUT is being exercised by the tester correspond to variations in the index of refraction profile through the DUT over time. A repetitive test signal may be applied to the DUT so that time sampling techniques and signal averaging techniques may be used.

Figure 5:
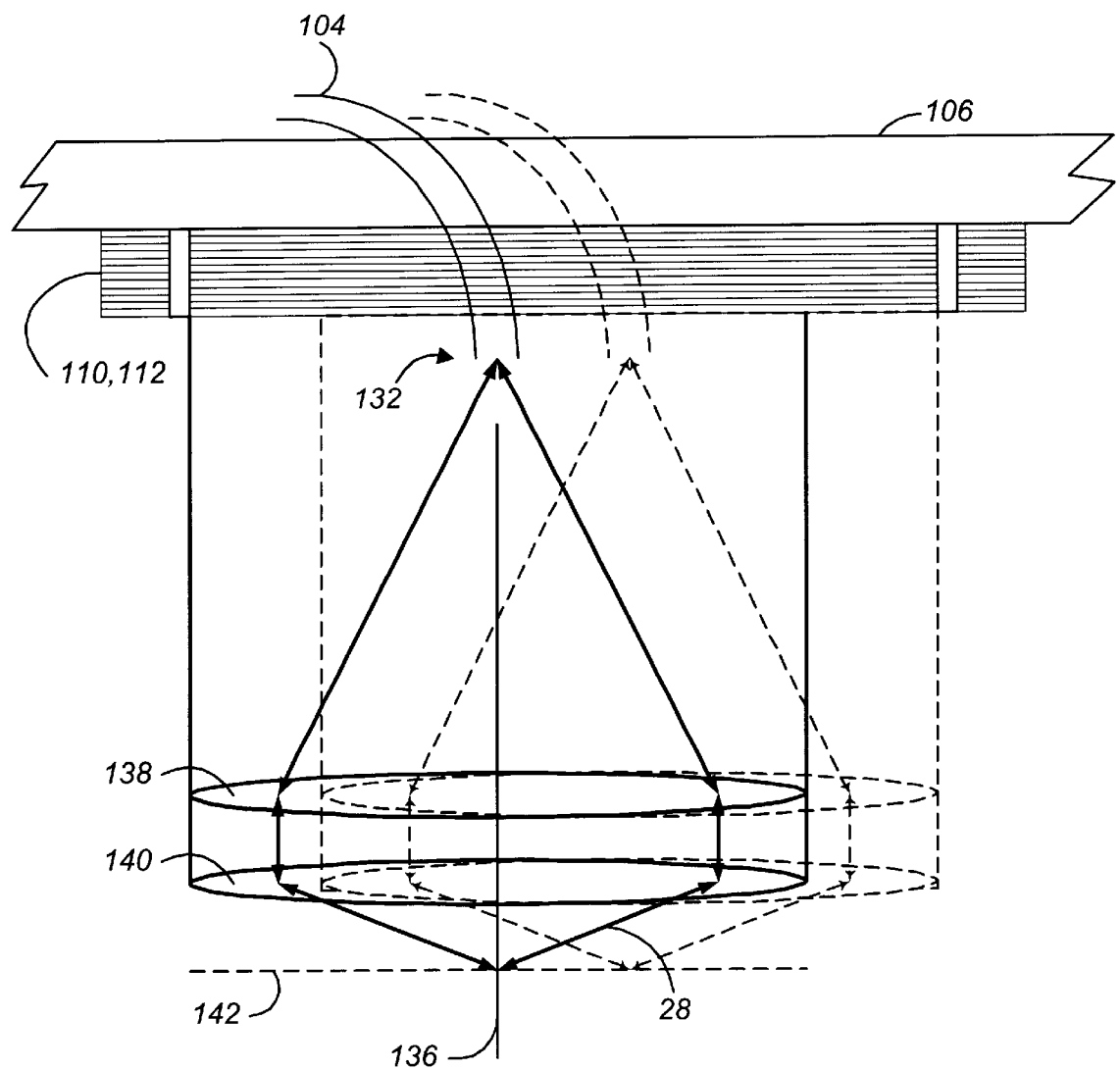
FIG. 5 is a schematic diagram of the imaging module at different times during a raster scan operation when the optical fiber and the optics are moved.

An image may be formed by raster scanning the optics 114 over the DUT (illustrated in FIG. 5). Scan generator 152 outputs a raster scan pattern which is amplified by high voltage amplifiers 154 to produce a signal that drive the coarse X-Y-Z stage 110 and fine X-Y-Z scanner 112 to scan the optics 114 over the DUT in a raster scan pattern. Scan generator 152 also sends signals to the frame grabber 158 so that the video display may be synchronized with the scan pattern. In one implementation, a coarse X-Y-Z stage 110 is driven by Newport CMA-25PP motorized actuators controlled through a Newport ESP300 controller, both of which are available from Newport Corporation of Irvine Calif. A program running on a computer such as a personal computer can control the ESP300 through its IEEE 488 interface.

Alternatively, the beam 28 may be moved and an image may be formed by moving the end of the fiber 104 and leaving the position of the lenses 138 and 140—which make up the imaging optics—fixed relative to the platform of the coarse X-Y-Z stage. In this case the coarse X-Y-Z stage, but not the fine scanner, must be able to move the optics. In either case, the coarse X-Y-Z stage must be able to move the fine scanner.

To create an image, the end 132 of a single-mode fiber 104 may be scanned with an X-Y stage 146 in a conjugate focal plane 148 in a demagnified raster scan pattern. This alternative provides a faster scan rate, as the fiber cable end is significantly lighter than the entire optics 114. Also, demagnification reduces the effects of the vibrations in the X-Y stage 146. On the other hand, because the scan is demagnified, the fiber end 132 must be scanned over a larger area than is required if the lenses moved with the fiber end, as described in reference to FIG. 3. For example, to image a 100 im×100 im field of view in the implementation shown in FIG. 3, the optics are scanned 100 im×100 im (1:1). In the alternative implementation, to scan the same 100 im×100 im field of view, the fiber end 132 would have to be scanned approximately 600 im×600 im.

In addition, the optics of in the alternative implementation must be corrected for off-axis illumination aberrations. For example, a suitable objective lens for the implementation is the Nikon A3717 available through Hamamatsu Corp. of Bridgewater, N.J. This 100× lens has a numerical aperture of 0.85 and a silicon correction ring, and provides a 100 im×100 im field of view. While this lens is also suitable for the implementation shown in FIG. 3, in the latter case the beam is always on axis, allowing a simpler, less expensive, and lighter weight objective to be used. Also, as described in reference to FIG. 3, a quarter-wave plate can be positioned between the fiber coupling lens 138 and the objective lens 140.

In another alternative, an extrafine scanner is fixed to the platform of the fine scanner, as are the imaging optics. The extrafine scanner moves the end of the fiber relative to the optics, and both the extrafine scanner and the optics are moved by the fine scanner.

Other embodiments are within the scope of the claims.

For example, a solid immersion lens may be coupled to the imaging module 16 to improve the resolution that may be achieved. The solid immersion lens can be attached to the objective lens or made positionable separately on the DUT. Low magnification lenses may be provided to assist in positioning the imaging module relative to the DUT. Multiple optical fibers may be used to transmit light to and from the imaging module. Beam splitters may be inserted in the imaging module between the collimating and objective lenses to create additional optical paths to or from the DUT, with collimating lenses for each additional optical path also being added to the imaging module. By fixing the further lenses and other elements defining the optical paths to each other and the fine scanner, as in the implementation shown in FIG. 3, or to the coarse stage, as in an alternative implementation, the advantages of the invention are obtained with respect to each optical path.

What is claimed is:

1. A optical probe system for optically probing an electrical device while operating the device under control of a tester of the kind operating to generate and apply a sequence of test vectors to the device and having a test head in which the device can be mounted, the optical probe system comprising:

a light delivery and imaging module having imaging optics and a fine scanner and being configured to be docked to a test head;

an optical processing subsystem operable to generate an incoming beam of light to illuminate the device;

a data processing subsystem operable to generate control signals for the module and operatively coupled to transmit control signals to the module, the fine scanner having a frame and a platform and being coupled to receive control signals from the data processing subsystem to move the platform relative to the frame; and an optical fiber connected to transmit the incoming beam from the optical processing subsystem to a fiber end in the module;

wherein the imaging optics have an optical axis, the fiber end is mounted in a fixed position on the optical axis so that light emitted from the fiber end is focused at a focal point in a focal plane by the imaging optics, and the fiber end and imaging optics are mounted in a fixed position to the platform of the fine scanner, whereby operating the fine scanner moves the fiber end, the imaging optics, the optical axis, and the focal point as a rigid unit.

2. The system of claim 1, further comprising:

a coarse stage having a frame and a platform, the platform being connected to the fine scanner in a fixed relationship, the coarse stage being coupled to receive control signals from the data processing subsystem to move the platform of the coarse stage.

3. The system of claim 1, wherein:

the fine scanner is operable to move the imaging optics and the fiber end in an XY plane perpendicular to the optical axis and in a Z direction parallel to the optical axis; and the fine scanner is so positioned in the module that the focal point moves in a focal plane intersecting the device when the fine scanner moves the fiber end in the XY plane and the module is docked to the test head.

4. The system of claims 1 or 3, wherein:

the fiber is a polarization-maintaining, single-mode fiber;

the incoming beam of light is monochromatic and linearly polarized; and the fiber end is polished so that the beam is spatially filtered.

5. The system of claims 1 or 2, wherein:

the focal point and the fiber end are conjugate focal points of the imaging optics; and the fiber end defines an aperture that delivers light to and from the imaging optics, whereby light delivered to the imaging optics through the aperture and light reflecting from the focal plane passes through the aperture.

6. The system of claim 1, wherein:

the optical processing subsystem comprises a polarizing beam splitter configured to pass light from a light source with a first polarization and to reflect light with a different polarization toward a detector, the optical processing subsystem being configured to deliver the light from the beam splitter to the fiber; and the imaging optics comprise a quarter-wave plate on the optical axis between the fiber end and the focal point.

7. The system of claim 1, wherein:

the fiber is a single-mode fiber; and the incoming beam of light is monochromatic.

8. The system of claim 7, wherein the incoming beam of light is produced by a pulsed laser and has a near infrared wavelength.

9. The system of claim 2, wherein:

the fiber is a polarization-maintaining, single-mode fiber;

the incoming beam of light is monochromatic and linearly polarized;

the fiber end is polished so that the beam is spatially filtered;

the system further comprises a coarse stage having a frame and a platform, the platform being connected to the fine scanner in a fixed relationship, the course stage being coupled to receive control signals from the data processing subsystem to move the platform of the coarse stage;

the focal point and the fiber end are conjugate focal points of the imaging optics;

the fiber end defines an aperture that delivers light to and from the imaging optics, whereby light delivered to the imaging optics through the aperture and light reflecting from the focal plane passes through the aperture;

the optical processing subsystem comprises a polarizing beam splitter configured to pass light from a light source with a first polarization and to reflect light with a different polarization toward a detector, the optical processing subsystem being configured to deliver the light from the beam splitter to the fiber; and the imaging optics comprise a quarter-wave plate on the optical axis between the fiber end and the focal point.

10. The system of claim 9, wherein:

the optical processing subsystem and the data processing subsystem are housed in a common probe system chassis.

11. A method for optically probing an electrical device, comprising:

operating the device;

providing imaging optics, the imaging optics having an optical axis and a focal point on the optical axis, the imaging optics positioned in a spatial relationship to the device so that the focal point intersects the device;

providing an aperture on the optical axis through which light is delivered to the imaging optics;

moving the aperture, the optical axis, and the imaging optics as a rigid unit to move the focal point to a reference point in the device; and providing a beam of light to the aperture and receiving reflected light from the device;

wherein the device is operated under a repeating sequence of test vectors.

12. A method for optically probing an electrical device, comprising:

operating the device;

providing imaging optics, the imaging optics having an optical axis and a focal point on the optical axis, the imaging optics positioned in a spatial relationship to the device so that the focal point intersects the device;

providing an aperture on the optical axis through which light is delivered to the imaging optics;

moving the aperture, the optical axis, and the imaging optics as a rigid unit to move the focal point to a reference point in the device;

providing a beam of light to the aperture and receiving reflected light from the device; and raster scanning the focal point over an area of the device while illuminating the device with light delivered through the aperture.

13. The method of claim 11 or claim 12, further comprising:

placing the aperture at a conjugate to the focal point and receiving the reflected light through the aperture.

14. An optical probe system for optically probing an electrical device while operating the device under control of a tester of the kind operating to generate and apply a sequence of test vectors to the device and having a test head in which the device can be mounted, the optical probe system comprising:

a light delivery and imaging module having imaging optics, a coarse stage and a fine scanner, and being configured to be docked to a test head;

an optical processing subsystem operable to generate an incoming beam of light to illuminate the device;

a data processing subsystem operable to generate control signals for the module and operatively coupled to transmit control signals to the module, the coarse stage and the fine scanner being coupled to receive control signals from the data processing subsystem; and an optical fiber connected to transmit the incoming beam from the optical processing subsystem to a fiber end in the module;

wherein:

the imaging optics have an optical axis, a focal plane, and a conjugate focal plane;

a frame of the fine scanner and the imaging optics are mounted in a fixed position relative to a platform of the coarse stage, whereby operating the coarse stage moves the imaging optics, the optical axis, and the frame of the fine scanner as a unit; and the fiber end is mounted on a platform of the fine scanner so that operating the fine scanner moves the fiber end in the conjugate plane and so that light emitted from the fiber end is focused in the focal plane by the imaging optics;

whereby operating the coarse stage moves the fiber end, the imaging optics, the optical axis, and the focal point as a unit, and operating the fine scanner moves the fiber end and focal point relative to the imaging optics.

15. The system of claim 14, wherein:

the fine scanner is operable to move the fiber end in an XY plane perpendicular to the optical axis and in a Z direction parallel to the optical axis; and the fine scanner is so positioned in the module that the focal point moves in a focal plane intersecting the device when the fine scanner moves the fiber end in the XY plane and the module is docked to the test head.

16. The system of claims 14 or 15, wherein:

the fiber is a polarization-maintaining, single-mode fiber;

the incoming beam of light is monochromatic and linearly polarized;

the fiber end is polished so that the beam is spatially filtered; and the fiber end defines an aperture that delivers light to and from the imaging optics, whereby light delivered to the imaging optics through the aperture and light reflecting from the focal plane passes through the aperture.

17. The system of claim 14, wherein:

the optical processing subsystem comprises a polarizing beam splitter configured to pass light from a light source with a first polarization and to reflect light with a different polarization toward a detector, the optical processing subsystem being configured to deliver the light from the beam splitter to the fiber; and the imaging optics comprise a quarter-wave plate on the optical axis between the fiber end and the focal point.

18. The system of claim 15, wherein:

the fiber is a polarization-maintaining, single-mode fiber;

the incoming beam of light is monochromatic and linearly polarized;

the fiber end is polished so that the beam is spatially filtered;

the fiber end defines an aperture that delivers light to and from the imaging optics, whereby light delivered to the imaging optics through the aperture and light reflecting from the focal plane passes through the aperture;

the optical processing subsystem comprises a polarizing beam splitter configured to pass light from a light source with a first polarization and to reflect light with a different polarization toward a detector, the optical processing subsystem being configured to deliver the light from the beam splitter to the fiber; and the imaging optics comprise a quarter-wave plate on the optical axis between the fiber end and the focal point.

19. A method for optically probing an electrical device, the method comprising:

operating the device;

providing imaging optics, the imaging optics having an optical axis and a focal plane, the imaging optics being positioned in a spatial relationship to the device so that the focal plane intersects the device;

providing an aperture through which light is delivered to the imaging optics, positioned so that light from the aperture is focused at a focal point;

moving the imaging optics in a plane parallel to the focal plane;

moving the aperture relative to the imaging optics to move the focal point to a reference point in the device; and providing a beam of light to the aperture and receiving reflected light from the device.

20. The method of claim 19, wherein:

the device is operated under a repeating sequence of test vectors.

21. The method of claim 19, further comprising:

raster scanning the focal point over an area of the device while illuminating the device with light delivered through the aperture.

22. The method of claim 19, further comprising:

placing the aperture at a conjugate to the focal point and receiving the reflected light through the aperture.

* * * * *